United States Patent
Shambroom et al.

(10) Patent No.: US 9,974,924 B2
(45) Date of Patent: *May 22, 2018

(54) LUCID DREAM STIMULATOR, SYSTEMS, AND RELATED METHODS

(71) Applicant: Aladdin Dreamer, Inc., Paradise Valley, AZ (US)

(72) Inventors: John R. Shambroom, Framingham, MA (US); Craig Russel Weiss, Paradise Valley, AZ (US)

(73) Assignee: Aladdin Dreamer, Inc., Paradise Valley, AZ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/638,869

(22) Filed: Jul. 14, 2017

(65) Prior Publication Data

US 2017/0304583 A1  Oct. 26, 2017

Related U.S. Application Data

(63) Continuation of application No. 15/137,136, filed on Apr. 25, 2016, now Pat. No. 9,737,683.
(Continued)

(51) Int. Cl.
*A61M 21/00* (2006.01)
*A61N 1/04* (2006.01)
*A61N 1/36* (2006.01)

(52) U.S. Cl.
CPC .......... *A61M 21/00* (2013.01); *A61N 1/0456* (2013.01); *A61N 1/0476* (2013.01); *A61N 1/0484* (2013.01); *A61N 1/36025* (2013.01); *A61M 2021/005* (2013.01); *A61M 2021/0027* (2013.01); *A61M 2021/0072* (2013.01); *A61M 2205/3569* (2013.01); *A61M 2205/3592* (2013.01); *A61M 2205/505* (2013.01); *A61M 2209/06* (2013.01); *A61M 2209/088* (2013.01); *A61M 2210/06* (2013.01); *A61M 2230/005* (2013.01); *A61M 2230/10* (2013.01); *A61M 2230/18* (2013.01); *A61M 2230/63* (2013.01)

(58) Field of Classification Search
CPC .......... A61M 21/00; A61M 2021/0005; A61M 2021/0055; A61M 2021/0072; A61M 21/02
USPC ...................... 600/26–28, 382, 383, 393, 394
See application file for complete search history.

(56) References Cited

U.S. PATENT DOCUMENTS

3,762,396 A  10/1973  Ballentine et al.
5,123,899 A  6/1992  Gall
(Continued)

OTHER PUBLICATIONS

International Search Report and Written Opinion for International Application No. PCT/US2016/030766, dated Jul. 11, 2016 (14 pages).
Voss et al., "Induction of self awareness in dreams through frontal low current stimulation of gamma activity," Nature Neuroscience, vol. 17, No. 6, Jun. 2014 (5 pages).
"Dream Fitness: How to Use Lucid Dreams for Weight Loss," (http://brainwavepowermusic.com/blog/blog/dream-fitness-how-to-use-lucid-dreams-for-weight-loss) last accessed May 4, 2016 (5 pages).
(Continued)

*Primary Examiner* — John Lacyk
(74) *Attorney, Agent, or Firm* — Bookoff McAndrews, PLLC (57) ABSTRACT

A dream stimulator may include a substrate and a plurality of electrodes positioned along a first side of the substrate. The stimulator also may include a stimulator coupled to the substrate. At least one lead may couple the plurality of electrodes to the stimulator. Additionally, a band may be positioned along a second side of the substrate and about each of the plurality of electrodes.

30 Claims, 8 Drawing Sheets

Related U.S. Application Data (60) Provisional application No. 62/158,521, filed on May 7, 2015.

(56) References Cited

U.S. PATENT DOCUMENTS

| | | |
|---|---|---|
| 8,239,030 B1 | 8/2012 | Hagedorn et al. |
| 8,268,851 B2 | 9/2012 | Kroll |
| 9,737,683 B2 * | 8/2017 | Shambroom ......... A61M 21/00 |
| 2004/0030258 A1 | 2/2004 | Williams |
| 2010/0041962 A1 | 2/2010 | Causevic et al. |
| 2014/0221779 A1 | 8/2014 | Schoonover et al. |
| 2014/0343354 A1 | 11/2014 | Larson |
| 2015/0343196 A1 | 12/2015 | Vasapollo |

OTHER PUBLICATIONS

Adee, Sally, "Zap your brain into the zone: Fast track to pure focus," New Scientist, Feb. 2012 (6 pages).

"Lucid Dreaming FAQ," Lucidity Institute, accessed from Lucidity.com, (last modified Feb. 16, 2015 ) (20 pages).

Marcus, A. D., "The Weird World of Brain Hacking," WSJ Online, (Nov. 9, 2015) (4 pages).

RunPhones, "Running Headband Headphones." RunPhones.com (last accessed Jan. 16, 2017) (4 pages).

* cited by examiner

LUCID DREAM STIMULATOR, SYSTEMS, AND RELATED METHODS

CROSS-REFERENCE TO RELATED APPLICATIONS

This application is a Continuation of U.S. patent application Ser. No. 15/137,136, filed on Apr. 25, 2016, which claims the benefits of priority from U.S. Provisional Application No. 62/158,521, filed on May 7, 2015, both of which are incorporated herein by reference in their entireties.

TECHNICAL FIELD

Various aspects of the present disclosure relate generally to systems, devices, and related methods for inducing lucid dreams. More specifically, the present disclosure relates to devices, systems, and methods for stimulating portions of a subject to induce a lucid dream state.

BACKGROUND

During sleep, human beings typically enter rapid eye movement (REM) sleep (e.g., dream sleep) during approximately 25% of their overall sleep time. During an average life-expectancy, one could expect to sleep for approximately 20 years and dream for approximately 5 years. While the vast majority of people experience dreams passively as a quasi-random set of experiences that happen to them and over which they have very little, if any, control, some people experience lucidity during their dream state. A lucid dream is a state in which one becomes aware that one is dreaming, and in many cases, they can control the dream experience. The ability to regularly have lucid dreams is quite rare. Some people, through the use of various mental exercises, are capable of inducing a lucid dreaming experience, though this often requires extensive practice and concentration, and even still only results in occasional lucid dreams.

During typical REM sleep, one experiences a primary state of consciousness that is concerned only with the immediate present. During wakefulness, human beings experience a secondary state of consciousness that introduces higher order cognitive functions such as self-reflective awareness, abstract thinking, and access to thoughts of both past and future. One way to think of lucid dreaming is as a state of sleep in which both primary and secondary states of consciousness exist simultaneously which allows the subject to become aware of the fact that he or she is dreaming during the dream. This awareness or lucidity can also provide the subject with the ability to exert control over the ongoing dream plot.

SUMMARY

Examples of the present disclosure relate to, among other things, systems, devices, and methods for inducing a lucid dream state in a subject. Each of the examples disclosed herein may include one or more of the features described in connection with any of the other disclosed examples.

In one aspect, a dream stimulator may include a substrate and a plurality of electrodes positioned along a first side of the substrate. The stimulator also may include a stimulator coupled to the substrate. At least one lead may couple the plurality of electrodes to the stimulator. Additionally, a band may be positioned along a second side of the substrate and about each of the plurality of electrodes.

Examples of the stimulator may additionally and/or alternatively include one or more of the following features. The substrate may be flexible to permit the substrate to attain a curved shape, and the substrate may include an adhesive. The plurality of electrodes may include four electrodes aligned on an axis of the substrate, and the plurality of leads may include four leads, each of the four leads corresponding to one of the four electrodes. The electrodes and the leads may be printed on the substrate. The band may include a flexible fabric that covers an entirety of the substrate. The substrate may include a first coupling mechanism having a shape corresponding to a shape of a first coupling feature of the stimulator, and the band may include a second coupling mechanism having a shape corresponding to a shape of a second coupling feature of the stimulator. The first coupling mechanism may include a plurality of posts and the first coupling feature may include channels. The stimulator also may include a sensor for measuring a physiological parameter of a subject.

In another example, a method for optimizing dream stimulation may include positioning a plurality of electrodes on a forehead of a subject. The method also may include delivering transcranial stimulation to the subject via the plurality of electrodes at a first frequency. Additionally, the method may include ceasing delivery of transcranial stimulation at the first frequency, monitoring brain activity of the subject, and delivering transcranial stimulation to the subject via the plurality of electrodes at a second frequency, different than the first frequency.

Examples of the method may additionally and/or alternatively include one or more of the following features. Monitoring brain activity may include sensing a frequency of electrical activity of the subject's brain via a sensor and the second frequency may correspond to a frequency of electrical activity sensed via the sensor. Monitoring brain activity may include determining whether a portion of the brain associated with dreaming has been stimulated to a predetermined level. The method also may include receiving feedback from the subject as to whether or not the subject had a lucid dream, and the sensed frequency may be based, at least in part, on the feedback. Delivering transcranial stimulation to the subject via the plurality of electrodes at at least one of the first frequency or the second frequency may include delivering a stimulation waveform including two or more frequencies. Additionally, the method may include delivering transcranial stimulation via the plurality of electrodes at the first frequency at pre-programmed intervals and wherein the first frequency is between 25 Hz and 40 Hz. The method also may include determining whether the subject has entered a Rapid Eye Movement (REM) sleep period, prior to delivering transcranial stimulation at the first frequency.

In another example, a method for optimizing dream stimulation may include positioning a plurality of electrodes on a head of a subject and delivering transcranial stimulation to the subject via the plurality of electrodes at a first frequency. The method also may include ceasing delivery of transcranial stimulation at the first frequency and determining a change of frequency of brain activity of the subject from the first frequency towards a natural frequency. Further, the method may include delivering transcranial stimulation to the subject via the plurality of electrodes at the natural frequency.

Examples of the method may additionally and/or alternatively include one or more of the following features. The method may further include delivering visual or audio content relating to a topic prior to delivering transcranial stimulation at the first frequency or the natural frequency. Also, the method may include delivering transcranial stimulation via the plurality of electrodes at the first frequency at pre-programmed intervals, and wherein the first frequency is between 20 Hz and 60 Hz. The method also may include determining whether the subject has entered a Rapid Eye Movement (REM) sleep period, prior to delivering transcranial stimulation at the first frequency. The method may include sensing a physiologic parameter of the subject, and ceasing delivery of transcranial stimulation at the natural frequency based on the sensed physiological parameter.

In another example, a method for optimizing dream stimulation may include positioning a plurality of electrodes on a forehead of a subject. The method also may include delivering transcranial stimulation to the subject via the plurality of electrodes at a first frequency. Further, the method may include delivering transcranial stimulation to the subject via the plurality of electrodes at a second frequency, different than the first frequency. In addition, delivering transcranial stimulation to the subject via the plurality of the electrodes at a first frequency may be performed simultaneously with delivering transcranial stimulation to the subject via the plurality of the electrodes at the second frequency.

It may be understood that both the foregoing general description and the following detailed description are exemplary and explanatory only and are not restrictive of the features described herein. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" as used herein is used in the sense of "example," rather than "ideal."

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 8-12B illustrate various views of an additional stimulator device, according to further aspects of the disclosure.

DETAILED DESCRIPTION

A lucid dream stimulator device 10 (or a plurality of devices 10 in combination as described below) and method capable of stimulating the lucid dreaming state is provided. Significant utility is achieved by portable lucid dream stimulator device 10, which may be comfortably worn by a subject while sleeping. For example, device 10 may be worn and used by the subject himself or herself, at home, without medical professional supervision. That is, the device 10 may be easily and conveniently worn by the subject in the subject's preferred environment (e.g., home, hotel, family or friend's home, etc.) and at a convenient time for the subject.

Figure 1:
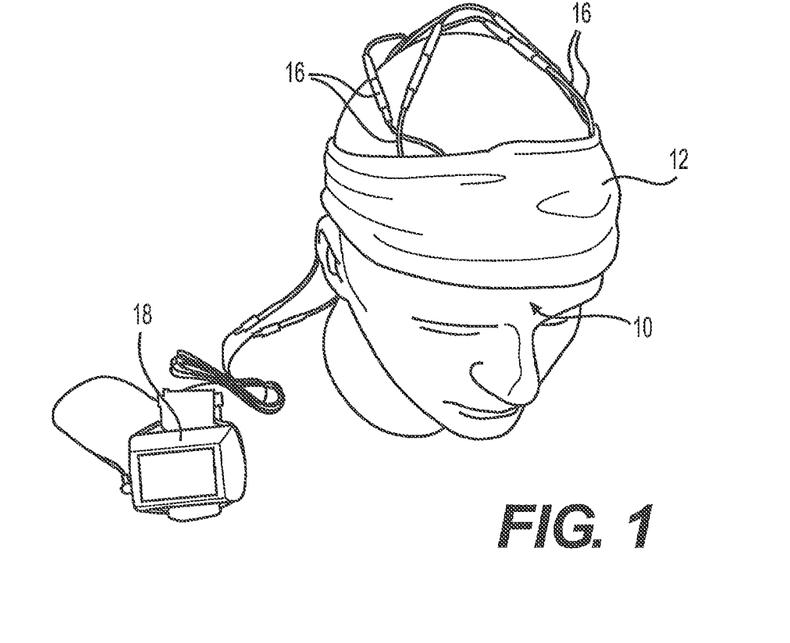
FIG. 1 illustrates an exemplary lucid dream stimulator device positioned on a model of a head.

Device 10 may include a head-worn portion as shown in FIG. 1. Device 10 may include a band 12 and a plurality of electrodes 14 (FIG. 2) coupled via electrical leads 16 to a source of stimulation 18. Band 12 may include an elastic, stretchable, or otherwise conformable strip of material (e.g., fabric). In some arrangements, band 12 may be comprised of a "breathable," light-weight, and/or loose-knit fabric so as to avoid excessive perspiration by the subject. Band 12 may be arranged so as to cover, surround, or otherwise maintain electrodes 14 in contact with the subject during use. For example, band 12 may prevent electrodes 14 from being dislodged from desired positions on the subject during use (e.g., during adjustment, shifting, turning, etc.).

Figure 2:
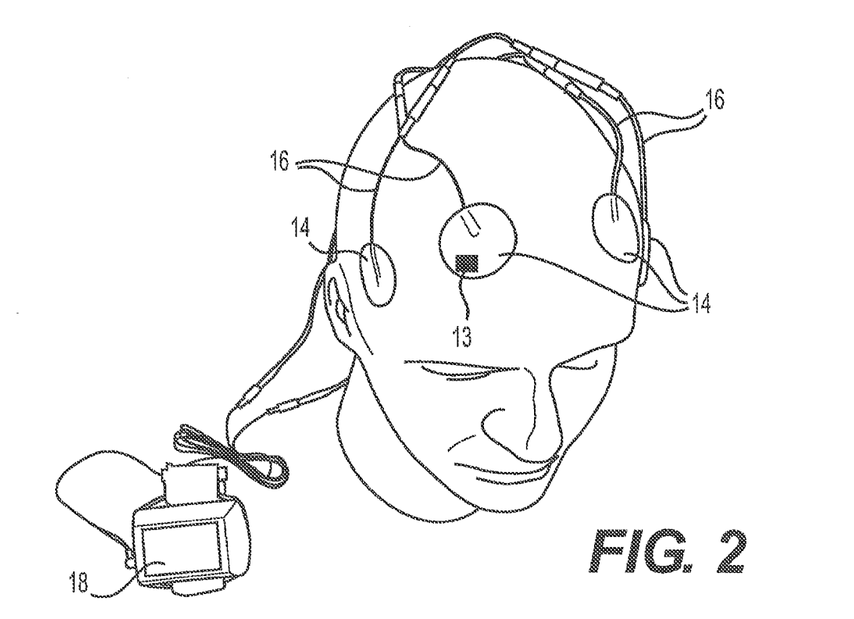
FIG. 2 illustrates a view of the exemplary lucid dream stimulator device of FIG. 1, in which a headband of the stimulator device has been removed.
Figure 7A:
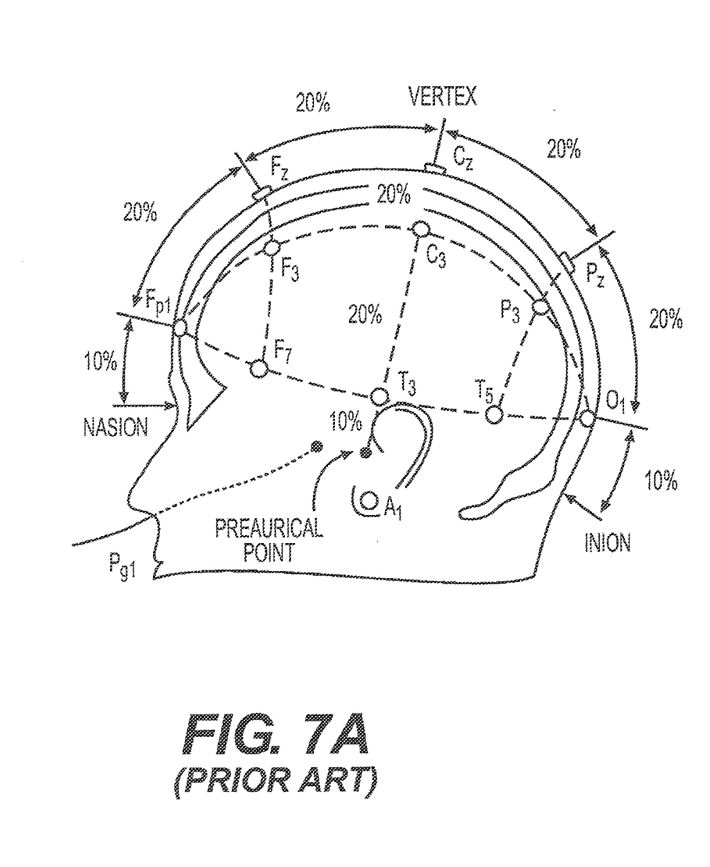
FIGS. 7A and 7B illustrate the international 10-20 system for electrode placement on the scalp.
Figure 7B:
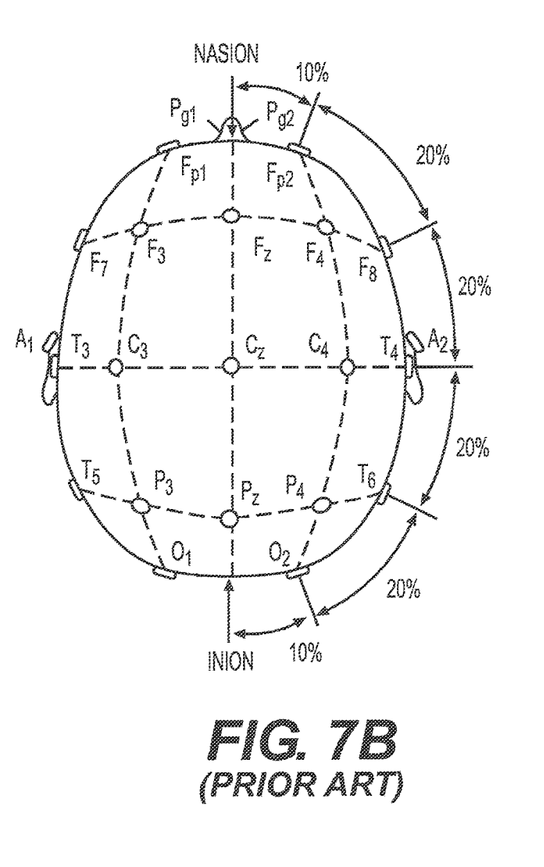

Electrodes 14 may include an adhesive on one or more portions or sides of electrodes 14. Accordingly, electrodes 14 may be supplied with a removable liner thereon to prevent inadvertent adhesion to one or more portions of the subject or device 10. Electrodes 14 may be arranged, as shown in FIG. 2, to provide electrical stimulation to at least one of the temporal and frontal areas of the brain of the subject. A standardized international 10-20 system for defining electrode 14 locations on the scalp is shown in FIGS. 7A and 7B. The system defines the locations based on the percentage of distance between certain fiducial points, including the nasion, the inion, and the overall circumference of the head. Positions are labeled F for frontal, C for central, P for parietal, O for occipital, and T for temporal, and are numbered front to back with odd numbers on the left and even numbers on the right. In instances in which intermediate positions are utilized, such positions are prefaced with the letter A. In the 10-20 system, electrode locations are defined as a percentage (either 10% or 20% depending on the location) of the circumference around the head, or the distance between certain anatomical features, namely the nasion and the inion. As such, electrode 14 spacing varies depending on the anatomy of a particular subject.

Figure 13:
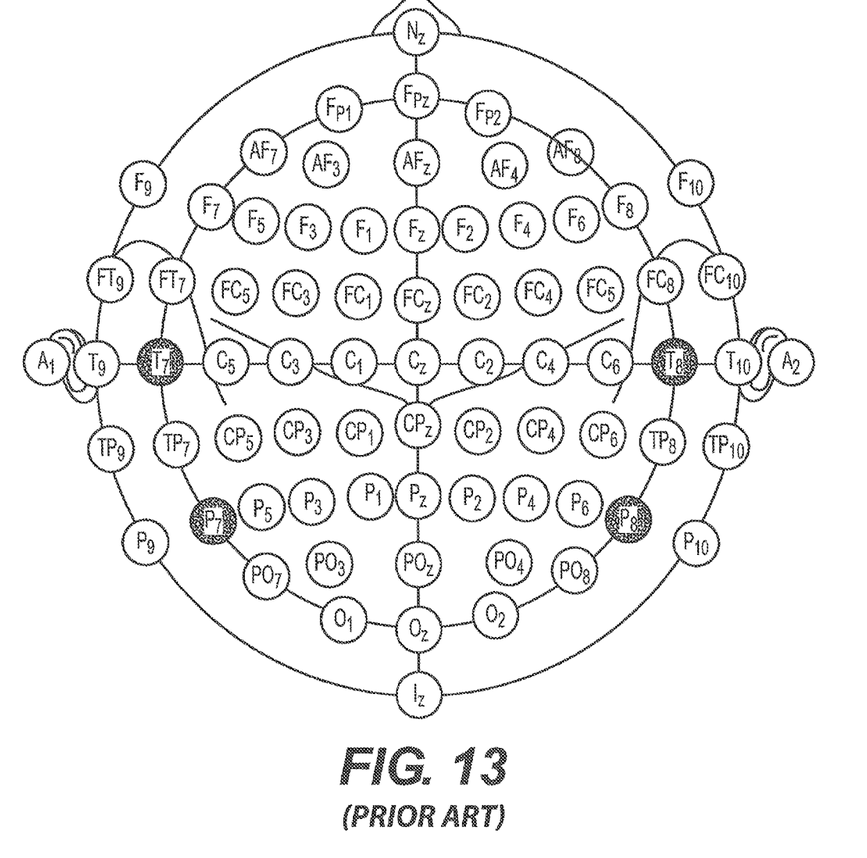
FIG. 13 illustrates the international 10-10 system for electrode placement on the scalp.

Returning to FIG. 2, four electrodes 14 are positioned along the forehead and temples of the subject for delivery of trans-cranial stimulation localized to the frontal cortex. It is understood that while four electrodes 14 are illustrated, fewer or more electrodes 14 may be positioned for delivery of trans-cranial electrical stimulation of the subject's brain. In some arrangements, for example, between two and about ten electrodes 14 may be positioned on the subject without departing from the scope of this disclosure. As used herein, the terms "about," "substantially," and "approximately," may indicate a range of values within +/−20% of a stated value. In some arrangements, all electrodes 14 may be positioned on the forehead or temples of a subject. In the example shown in FIG. 2, two forehead electrodes 14 may be positioned proximate to a subject's hairline, with each electrode 14 being approximately above one of the subject's eyes, and within a distance of approximately 8 centimeters above the center of the eyes. In addition, two temple electrodes 14 may be positioned approximately along a center-line of the forehead, just inside the hairline, preferably not more than 18 centimeters apart. That is, electrodes 14 may be located at the F7, F3, F4, and F8 (left to right) locations according to the standardized 10-20 system depicted in FIGS. 7A and 7B. Alternatively, electrodes 14 may be located at intermediate locations identified in a higher special resolution 10-10 system (FIG. 13), including the F7, AF3, AF4, and F8 locations. As shown in FIG. 13, the AF3 position may be located midway between the Fp1 and the F3 locations, while the AF4 position may be located midway between the Fp2 and F4 locations. Electrodes may be located as close to these positions as possible while avoiding the hairy areas of the scalp. That is, in some arrangements, none of electrodes 14 are positioned behind the ears, for example, of the subject. In other arrangements, electrodes 14 may additionally or alternately be positioned in the mastoid and/or precuneus regions. Further, in some further aspects of this disclosure, electrodes 14 may be arranged for delivery of transcranial stimulation in the prefrontal cortex, including the dorsolateral prefrontal cortex. Additionally or alternatively, electrodes 14 may be arranged so as to induce electrical activity in the cuneus of a subject's brain. In such an arrangement, transcranial stimulation of different portions of the subject's brain may induce different effects.

The left and right hemispheres of the brain process information in different ways. The left hemisphere tends to be analytical, while the right hemisphere tends to be more creative. As such, stimulating each of the left and right hemispheres may have different effects. For example, stimulating just the left hemisphere may prompt the subject to analyze the content of a dream, and come to the conclusion that he or she is dreaming, one of the hallmarks of lucidity. Also, the hemispheres may be differently stimulated to induce different aspects in the dream, for example the optimization of right sided stimulation to enhance dream content may be different than optimization of the left side to promote awareness of dreaming. Optimization parameters may include, but are not limited to, timing, frequency, intensity. Since stimulation may differ between the left and right hemispheres, electrode 14 placement may not be symmetric about a centerline that divides the subject's head into hemispheres. Additionally, the number of electrodes 14 on each hemisphere may differ. For example, three electrodes 14 may be positioned on the left hemisphere while one electrode 14 may be positioned on the right hemisphere, or vice versa.

Figure 4:
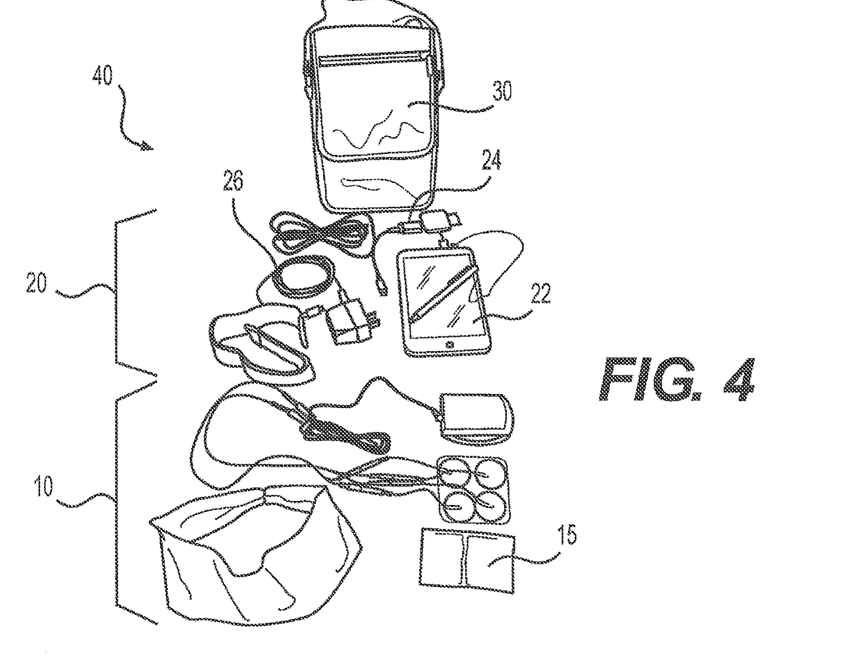
FIG. 4 illustrates an exemplary kit including the lucid dream stimulator device of FIG. 1.

Each electrode 14 may be disc-shaped as shown in FIG. 2. However, electrodes 14 may have any shape suitable for delivery of stimulation energy to the subject, such as, for example, rectangular, ovular, square, triangular, polygonal, or irregular shapes. In addition, electrodes 14 may have a size (e.g., area) of about 1.0 inches-square (6.5 cm$^2$) to about 4.0 inches-square (25.8 cm$^2$). In one exemplary arrangement, electrodes 14 may be circular and have a diameter of about 1.25 inches (31.75 mm). While each electrode 14 as shown in FIG. 4 is depicted as having a common shape and size, it is understood that at least one or more of electrodes 14 may have varied shapes and/or sizes without departing from the scope of this disclosure.

As noted above, electrodes 14 may be arranged for trans-cranial electrical stimulation to the frontal lobes of the brain. However, it should be clearly understood that substantial benefit could be derived from an alternative arrangement of the present disclosure in which electrical stimulation is provided by means other than through electrodes 14, such as through a conductive band or some other means. Further, in some arrangements, one or more of electrodes 14 may include a sensor 13 (schematically illustrated in FIGS. 2 and 3). Sensor 13 may measure one or more behavioral or physiological activities of the subject, such as what sleep stage the subject is in, or whether the subject is in REM sleep in particular. In other arrangements, however, such sensors 13 may be separate and discrete from electrodes 14. Sensor 13 may also measure or detect movement of the subject, and electrodes 14 may provide stimulation during only periods in which sensor 13 detects a lack of movement. Also, sensor 13 may measure or detect undesirable changes in physiological parameters (e.g., a large, predetermined increase in heart rate), and device 10 can be configured to cease stimulation upon that detection.

Figure 3:
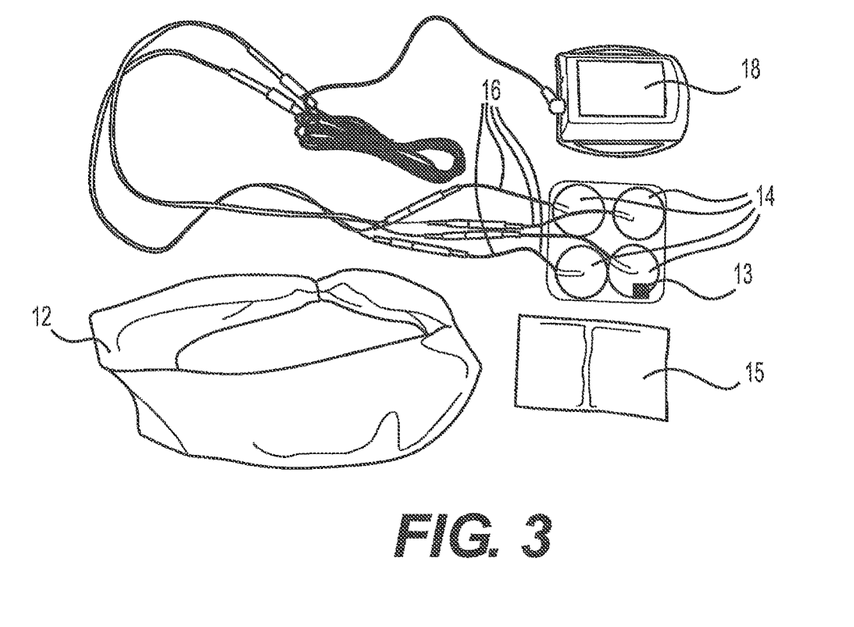
FIG. 3 illustrates components of the exemplary lucid dream stimulator device of FIG. 1 uncoupled from the model of a head.

As shown in FIGS. 1-3, electrodes 14 are coupled to a stimulator 18 via one or more electrical leads 16. Electrodes 14 may be constructed from a conductive material such as stainless steel, copper, and/or tin, and may be plated with nickel or other materials. Electrodes 14 may be a laminate including a cloth backing, a conductive carbon layer, and a suitable conductive gel (e.g., hydro-gel). Electrodes 14 may include a sponge that when wetted with a salinated solution becomes conductive. Alternatively, electrodes 14 may be incorporated onto a common substrate (e.g. substrate 60 shown in FIGS. 9-12B). The substrate 60 may be made of mylar, polyester, or other suitable material. Optionally, electrodes 14 may be printed on the substrate 60. Printing materials may include silver ink, silver/silver-chloride, copper, conductive carbon, or other such conductive materials. Additionally, a suitable conductive liquid or gel can be incorporated. Leads 16 may be printed on the substrate as well using any suitable conductive material (FIG. 11), as will be described in further detail below.

Stimulator 18 may be any appropriate stimulation source for delivery of electrical energy to electrodes 14. For example, stimulator 18 may include a Transcutaneous Electrical Nerve Stimulation (TENS) device. Stimulator 18 may be battery-operated or may draw energy through a household electrical outlet. Stimulator 18 may include an electronics module (not shown) and may generate and deliver current through leads 16 to electrodes 14 for delivery to the subject. Stimulator 18 may be configured to modulate pulse width, frequency, and intensity to suit a particular application or subject's preferences. The electronics module of stimulator 18 may include a wireless chip or other such device for wirelessly communicating with a tablet 22, as described in further detail below. Stimulator 18 may be configured for Transcranial Direct Current Stimulation (tDCS). In some arrangements, however, stimulator 18 may be configured for Transcranial Alternating Current Stimulation (tACS). It has been observed that tACS may enable improved effectiveness and specificity of stimulation via electrodes 14.

In arrangements in which stimulator 18 is configured for delivery of tACS, the electrical current delivered from stimulator 18 may flow into the body of the subject through one or more electrodes 14, and out of the body of the subject through one or more different electrodes 14. Unlike Transcranial Direct Current Stimulation (tDCS), which has a defined polarity, and therefore, both a cathode and anode electrode, tACS has alternating polarity. Therefore, the electric field and consequent effect on the brain region under each electrode 14 is more or less equivalent.

Figure 5:
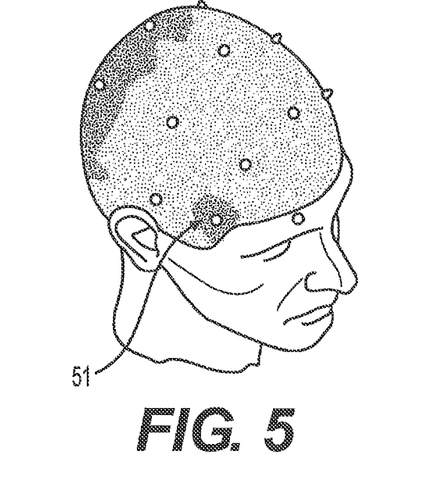
FIG. 5 is a visual representation of the brain activity observed during spontaneous lucid dreaming.

Arrangements of the present disclosure may improve, or adjust locations of, brain activity during lucid dreaming. For example, FIG. 5 illustrates brain activity zone 51 (e.g., relative electrical activity) observed during spontaneous lucid dreaming, e.g., lucid dreaming without electrical stimulation. As shown, brain activity zone 51, having a relatively higher localized electric activity, is lateral to the temples of the subject. The occipital area of the head, in particular the cuneus, is also displaying higher localized activity, which may be due to an increase in activity of the visual cortex.

Figure 6A:
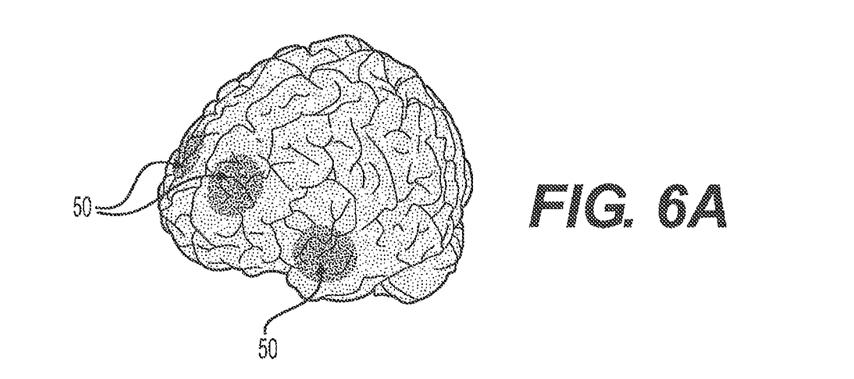
FIGS. 6A and 6B illustrate visual representations of the concentration of stimulation produced in a subject via the lucid dream stimulator of FIG. 1, when the stimulation is delivered to the subject in a variety of locations.
Figure 6B:
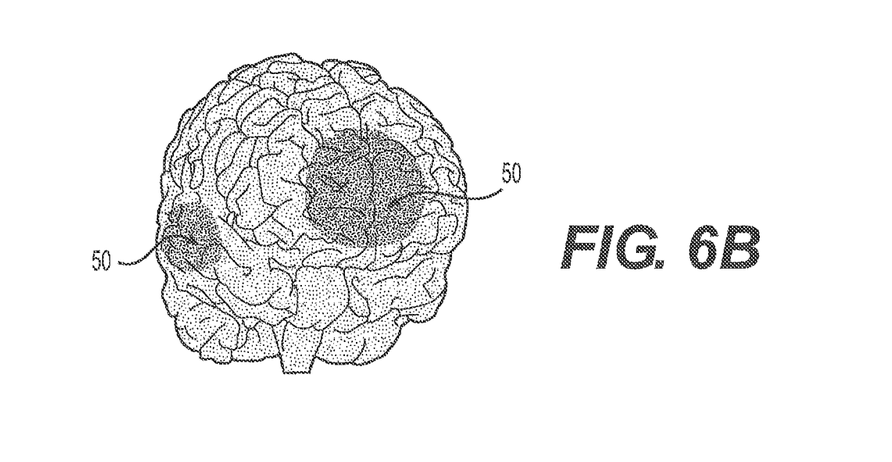

FIGS. 6A and 6B illustrate the brain stimulation zone 50 produced in a subject via the device 10 of FIG. 1, when stimulation is delivered to the subject in a variety of locations. For example, in the arrangement of FIG. 6A, four electrodes 14, including a pair of interconnected electrodes 14 may be located at the AF3 and AF4 locations, with interconnected return electrodes 14 located at the F7 and F8 locations. In such an arrangement, the stimulated potentials are relatively higher at the two frontal locations just lateral to the midline under positions AF3 and AF4, as shown in FIG. 6A. Likewise the left and right (not shown) fronto-temporal regions exhibit relatively higher potential under electrodes 14 at positions F7 and F8, as shown in FIG. 6A. In an additional arrangement, three electrodes 14, including a single electrode 14 located at the Fpz location (e.g., midway between the Fp1 and Fp2 locations) (FIG. 13), or alternatively at the AFz location (e.g., midway between the Fpz and the Fz locations) (FIG. 13), and return electrodes 14 may be located at the F7 and F8 locations. In such an arrangement, the stimulated potentials are relatively higher at the frontal location near the midline, as shown in FIG. 6B. Likewise the right and left (not shown) fronto-temporal regions exhibit relatively higher potential under electrodes 14 located at the F7 and F8 positions, as shown in FIG. 6B. As shown, stimulation potential of stimulation zone 50 of FIG. 6B is larger or wider spread than brain activity or stimulation zone 50 of FIG. 6A. Stimulation with electrodes 14 at the locations described in connection with FIG. 6A may be preferred since such an arrangement results in stimulation of the targeted, specific, or limited areas that become active during spontaneous lucid dreaming (e.g., as shown in FIG. 5). However, stimulation with electrodes 14 at the locations described in connection with FIG. 6B may be preferred because the larger inter-electrode 14 distance may enable the stimulus current to travel deeper into the brain, eliciting a more vigorous response in some subjects. While the above description details positioning of electrodes 14 along certain points of a subject's scalp, it is to be understood that these locations may vary from person to person depending on the anatomy, size, or features of an individual subject's scalp. Accordingly, in some arrangements, electrodes 14 may not be positioned precisely on the locations identified by the 10-20 or 10-10 systems. In such an arrangement, electrodes 14 may be located as closely as possible to the identified positions, while remaining out of the hairline of the subject. Further, while the above noted electrode 14 positions are described, the disclosure is not so limited. Rather, electrodes 14 may be positioned in other arrangements, such as on the mastoid of a subject. In such an arrangement, electrodes 14 may be positioned at the A1 and/or A2 locations (e.g., the earlobes), as identified in both the 10-20 and 10-10 systems. However, it is understood that in some arrangements, electrodes 14 may be positioned on the bony joint just behind the ears of a subject. Such positions may be identified as the M1 and M2 locations (not shown).

In one exemplary arrangement, device 10 may provide electrical stimulation in the gamma frequency band, between about 10 Hz and about 100 Hz, for example, between about 20 Hz and about 60 Hz, or between about 25 Hz and about 40 Hz. During a subject's dream state, this frequency range may activate, excite, or otherwise stimulate the executive ego functions (e.g., self-awareness) that are also observed during wakefulness. The optimal frequency for eliciting these effects may differ from subject to subject, e.g. it could be about 42 Hz for one subject and about 38 Hz for another subject. It is therefore advantageous for the device 10 to optimize the frequency for the individual user. This can be done by stimulating at a particular frequency and gauging the effects. The effect may be assessed by soliciting feedback from the user as to whether or not they had a lucid dream. Alternatively, a sensor could measure electrical activity of the brain before, during, or after stimulation to assess the effects. The excitation frequency could be adjusted to improve effectiveness. In addition, stimulation in the high beta band may impart a sense of control over the storyline or actions in a dream, for example at or near an excitation frequency of about 25 Hz. In a preferred arrangement, the stimulation waveform may incorporate two or more frequencies to potentiate multiple effects. It should be understood that while a stimulation frequency range between about 10 Hz and about 100 Hz, a stimulation frequency range between about 20 Hz and about 60 Hz, and/or a stimulation frequency range between about 25 Hz and about 40 Hz, may be particularly useful, substantial benefits may be derived from an alternative arrangement in which the stimulation frequency deviates, even substantially, from the above-noted frequency ranges.

In one exemplary arrangement, device 10 may alter the frequency during stimulation. For example, a certain subject's optimum stimulation frequency may be unknown. Device 10 may alter the frequency around the typical or average frequencies known to induce lucid dreaming in a sample of subjects. Device 10 may begin stimulation at 38 Hz for 5 seconds, then move to 39 Hz for 5 seconds, and so on until it finishes stimulating at 42 Hz.

In use, the subject may clean a surface area of skin prior to application of electrodes 14 on the subject. For example, in order to remove dirt, oil, and/or dead skin, which may impede delivery of energy via electrodes 14, the subject may wash, exfoliate, and/or sterilize the skin. For example, the subject may use one or more alcohol pads 15 to clean the skin. With proper cleansing, impedance to each electrode 14 may be reduced to between about 5 kΩ and about 100 kΩ. In addition, to facilitate efficient delivery of energy via electrodes 14, an area of skin may be wet or otherwise lubricated with an electrically conductive material. Such materials may include saline, water, and/or hydrogel.

Device 10 may be configured to determine when the subject has entered a REM (Rapid Eye Movement) period. As such, device 10 may be configured to activate electrical stimulation via electrodes 14 only during periods (or parts of periods) of REM sleep. Determination of whether the subject is in REM sleep may be accomplished by sensor(s) 13 which may be positioned on, adjacent, or otherwise near electrodes 14. However, substantial benefit may be provided by an alternative arrangement in which either there is no REM monitoring, or in which assessing REM sleep is accomplished by some other means, such as a sleep mask capable of using IR or other sensors to detect rapid eye movement, and/or another sensor capable of detecting EEG sleep frequencies and/or muscle tone otherwise associated with REM sleep. In arrangements wherein REM monitoring is accomplished by a separate device, communication between the devices may be provided. The device also could be used without REM monitoring and instead provide the electrical stimulation at pre-programmed intervals or simply on a timer (e.g., so as to coincide with normal circadian times of REM sleep (e.g., 5-8 AM)).

The device 10 may be portable and wireless, and capable of being recharged by the subject when not in use (e.g., when the subject is not sleeping). In some arrangements, device 10 may be synced with a smartphone, tablet, smart watch, computer, or other electronic device or system 20 (FIG. 4) having an application capable of receiving and transmitting data wirelessly to device 10. In some arrangements, however, delivery and transmission of data may be done via a wired connection. By way of example only, the system 20 may include a tablet 22 (e.g., an iPad), a data transmission, downloading, or synching connection 24, and a power adaptor 26. As shown in FIG. 4, the entire system may be prepared and packaged as a kit 40 in a portable carrying case or bag 30. For example, kit 40 may include device 10, any required cleaning supplies (e.g., alcohol pads 15), and electronic system 20. The application of electronic system 20 not only would track the subject's sleep patterns, but may also instruct device 10 to vary the frequency and/or duration of the electrical stimulation to achieve a subject-specific optimal lucid dreaming experience. Such duration and frequency adjustments could be part of pre-programmed patterns established as optimal, or could be altered/adjusted by the subject based on their feedback. After awakening, the subject could provide input to device 10 either directly into a subject interface on stimulator 18 of device 10, or via tablet 22 specifying his/her sleep experience. The subject could answer questions relating to his/her dreams, length, and/or quality, and/or the subject could indicate specific technical adjustments (e.g., increase/decrease frequency/duration).

In an alternative arrangement, the device 10 may be powered by a subject's smartphone, tablet 22, or other personal computing device. In such an embodiment, electrodes 14 could be wired directly into a smartphone (e.g., via one or more of a headphone jack and power port such as USB or lighting, etc.) or device 10 could be recharged by the smartphone but still capable of wireless power when in use. In these embodiments, device 10 may comprise one or more electrodes 14 that may be placed on the subject's head and capable of being recharged (e.g., via a wall outlet, smartphone, etc.), or electrodes 14 could be wired directly to a smartphone, tablet 22, or other personal computing device that is capable of both providing power as well as enabling data communication.

Placement of the head-worn device on the subject and/or selection of a stimulation frequency level or range (as, for example, described herein) may also need to be adjusted on a subject-by-subject basis. Optimal placement may be achieved through subject customization achieved based on subject feedback, either directly into stimulator 18 of device 10 or through use of an application of electrical system 20 (e.g., via tablet 22). For example, a subject, after awakening, preferably would indicate to an application on their smartphone, tablet 22, computer, smart watch, or the like to indicate the quality of their sleeping and dreaming experience. Upon receipt of inputs, recommendations for adjustments to the number and/or placement of electrodes 14, stimulation frequency and/or amplitude, the times to initiate stimulation, and/or the duration of stimulation could be suggested automatically by the application until optimal placement and stimulation is achieved to provide maximal lucid dream induction and minimal sleep disruption.

It should also be understood that one or more portions (e.g., electrodes 14 and/or band 12) of device 10 may be disposable in nature, so that it could be used by a subject for as little as one night or perhaps between 1 week and 3 months. In this way, the subject could avoid the need to clean device 10 and instead simply dispose of it and replace it with a new device 10 if and when the contacts, electrodes 14, or some other aspect of device 10, such as band 12 or sleeping cap, became dirty. Alternatively, the areas of device 10 that make contact with the subject could be cleaned, and device 10 could be reused. This could be accomplished a number of ways, such as by having electrode 14 contacts be detachable and cleanable so that they could then be reattached following sterilization.

While device 10 may be designed for the induction of lucid dreaming, it is within the scope of this disclosure that other non-lucid-dreaming benefits may be achieved by the same device. For example, it may be possible to use device 10 and transcranial electrical stimulation to provide neurofeedback, Eye Movement Desensitization and Reprocessing (EMDR), bio-feedback, or other treatments.

A further arrangement may include the use of an application located on a smartphone, tablet 22, computer, smart watch, device 10 itself, or the like that can be used by the subject prior to use of device 10 to improve the lucid dreaming experience by allowing the subject to view various videos, images and/or text prior to initiating sleep. For example, a subject who is interested in having lucid dreams about Venice, Italy could view videos, images, text, music or other content relating to Venice prior to sleep, which in combination with device 10 could improve the lucid dreaming experience. Another example might be for a subject interested in having one more lucid dreams in which the subject can fly. In such a scenario, the subject could watch content relating to flying. If someone wishes to see or meet with someone (alive or dead) during their dream, they could view content relating to that person (e.g., Albert Einstein, President of the U.S., a deceased loved one, etc.). To that end, the subject could customize the application to load their own content (e.g., pictures of a loved one). In a preferred embodiment, the application would have a social networking component in which other subjects could post their own content for use by others. For example, a subject who just finished mountain climbing could post video of their exploits in order for another subject to have images that could be incorporated into their lucid dream. It should be understood that the application concept described herein, including the social networking aspect, could be used separate and apart from device 10 as a method for improving one's dream experience.

In addition, an application of electrical system 20 could provide content for a guided meditation, sounds that evoke specific memories or images, instruction, or other audio content that the subject could listen to immediately preceding, or during, sleep to achieve a positive and desired lucid dreaming state. Such content could also be integrated into one or more portions of device 10 itself (e.g., electrodes 14, band 12, etc.), either stored locally on the device or streamed to device 10 from another device. In this arrangement, device 10 may have speakers, headphones, ear buds or the like, or alternatively, audio equipment could be provided separately and used in conjunction with device 10.

In order to induce lucid dreaming of a subject, electrical stimulation may be provided to at least one of the frontal, temporal, mastoid, and precuneus regions (e.g., lobes) of the subject's brain during REM sleep. Providing such electrical stimulation may include positioning a device (e.g., sensor 13 or other such device) capable of detecting when a subject enters REM, using the indication that the subject has entered REM to initiate electrical stimulation via electrodes 14 for at least some period of the REM sleep period, and terminating the electrical stimulation once it is detected that the subject is no longer in REM sleep.

There are a variety of benefits associated with lucid dreaming. There are significant psychological and/or therapeutic benefits associated with consciousness in the dream state. For those with persistent nightmares, PTSD, schizophrenia or other emotional issues that manifest themselves in the dream state, the ability to take control over a negative dream experience and overcome nightmares can be very empowering, turning a negative emotional experience into a positive one. That is, a method may include improving "positivity" or reducing anxiety of one's dreams. As such, the method may include inducing lucidity in dreams, even if just awareness or dissociation without control, thereby enabling a subject to reduce anxiety associated with anxiety producing dreams (e.g., an overachiever dreaming of being unprepared for an examination, etc.). Awareness that the anxiety causing dream is not reality may immediately reduce anxiety.

In some exemplary arrangements, one or more portions of device 10, such as sensors 13 or electrodes 14, may enable bio-feedback of physiological responses to stimulation. For example, a method may include an initial stimulation via electrodes 14 to induce a lucid dream state in a subject at a pre-determined frequency, e.g., 25 Hz. Next, the initial stimulation may be discontinued, and brain activity may be monitored via, for example, sensors 13 and/or electrodes 14 to determine whether the subject's brain organically (e.g., naturally) migrates toward a different frequency (e.g., 24 Hz, 26 Hz, 40 Hz, etc.) other than the frequency of the initial stimulation. Then, the next stimulation by device 10 may be calibrated to be delivered at the frequency the subject's brain migrated towards. That is, device 10 may recalibrate itself to best suit each individual subject's biological preferences. Such recalibration may be effective to improve inducement of lucid dreaming in the subject. In other words, the device may "jump-start" brain activity in portions of the subject's brain (e.g., the temporal-frontal cortex), then cease stimulation and monitor brain activity in order to determine the subject's own individual optimal brain frequency, and then adjust as appropriate to stimulate at the optimal brain frequency identified. As such, device 10 may maintain lucidity as naturally as possible for an individual subject.

In another exemplary method, the subject may be prompted to or independently think of certain subject matter, such as, for example, calming memories or thoughts. The subject may then use a smartphone, tablet 22, computer, device 10 itself, or the like to view visual feedback. Such visual feedback may include, for example, dynamically moving colored lights or other such visual displays. The subject's brain wave pattern may be monitored through any appropriate means (e.g., sensors 13 or the like). If the subject's brain wave pattern strays from the preferred or optimal pattern (e.g., the calming memories or thoughts), then the subject may receive visual (i.e. bio) feedback of a different sort, for example, black and white images, less or not dynamic, smaller, etc. Such a method enables the subject to condition their brain waves to the preferred/optimal patterns. Use of bio-feedback in device 10 may be applicable for the treatment of a wide array of conditions including, for example, insomnia, depression, anxiety, etc. Such conditions may or may not be directly related to lucid dream stimulation.

Another benefit to lucid dreaming comes from the ability to practice or rehearse waking activities while in the dream state. This has been proven to improve performance of the same activity during the waking state, including recovery from injury and weight loss. Dreamers have been known to rehearse various activities, such as specific athletic activities, public speaking, playing a musical instrument, etc. Because brain activity during the dream state may be similar to brain activity during the waking state, neural pathways created during practice or activity can be established in the dream state in preparation for performance in the waking state.

Figure 8:
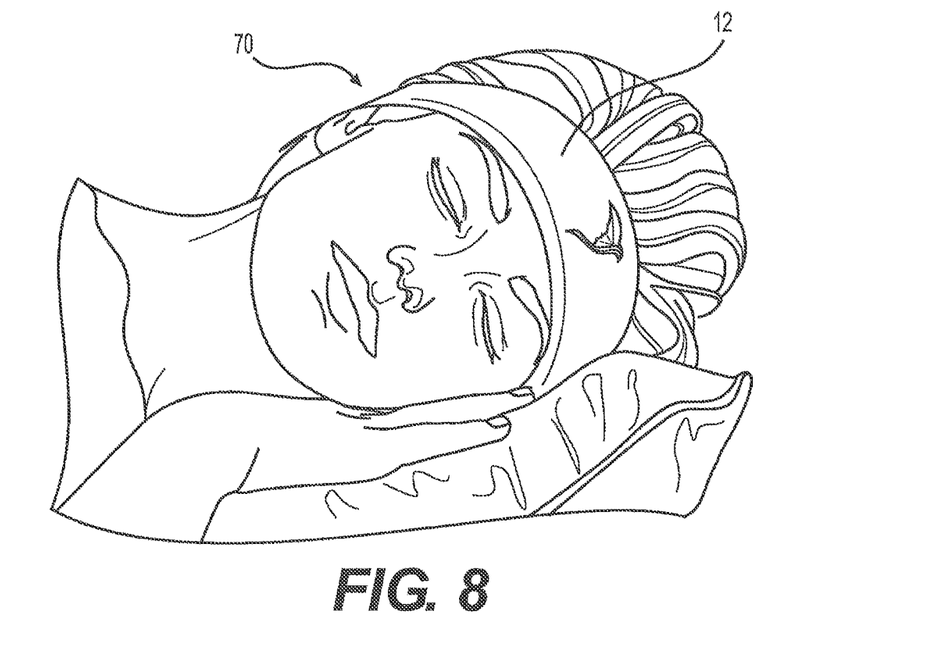
Figure 9:
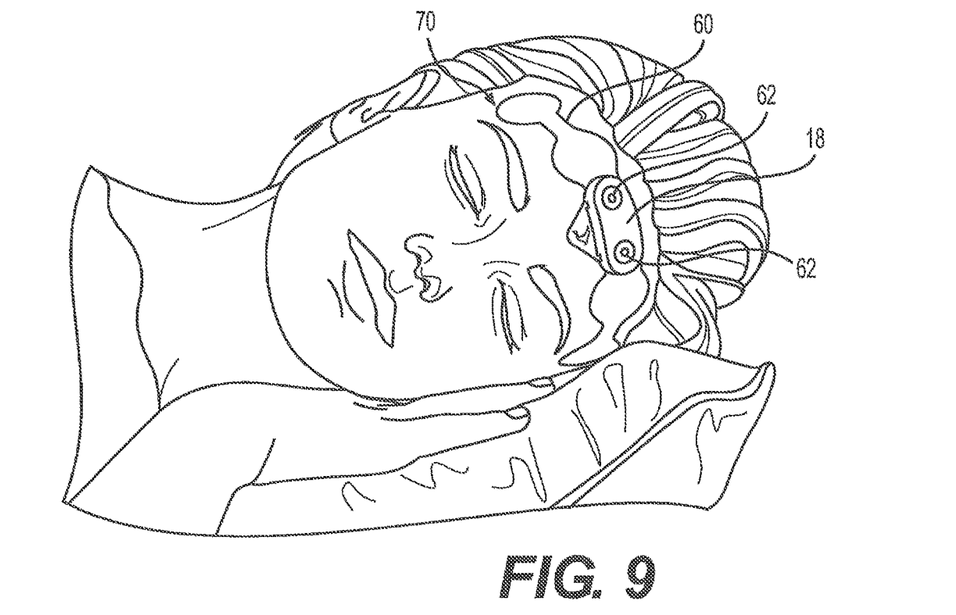
Figure 10:
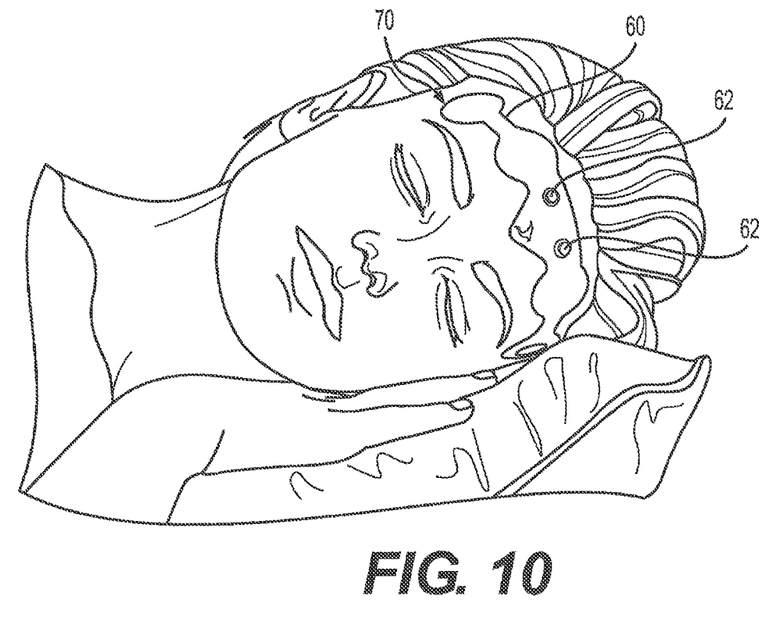
Figure 11:
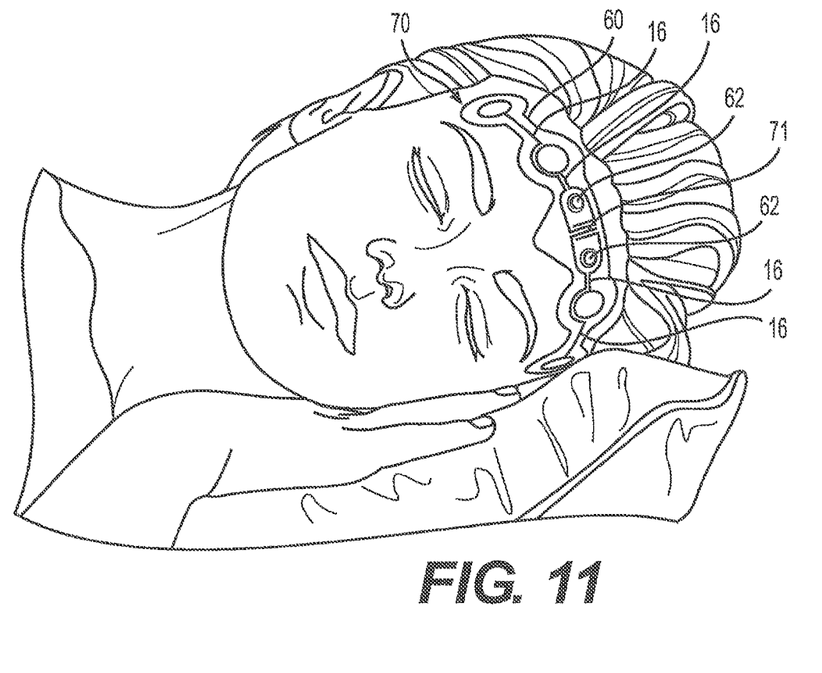
Figure 12A:
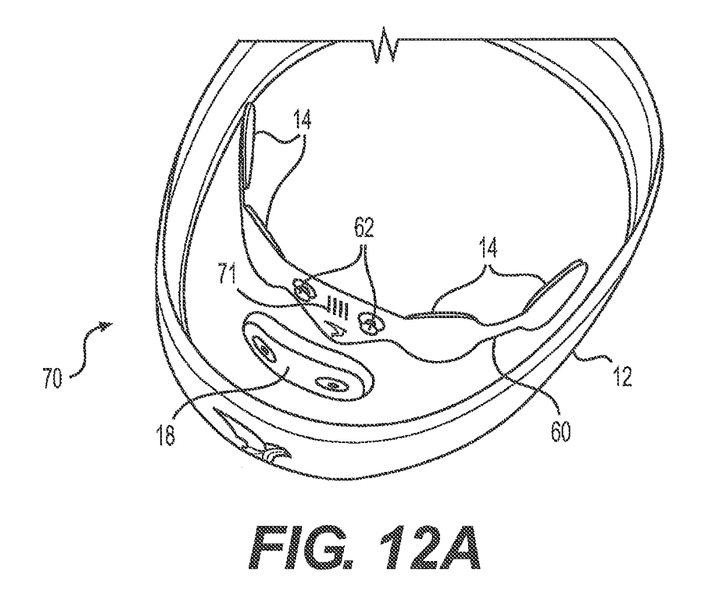
Figure 12B:
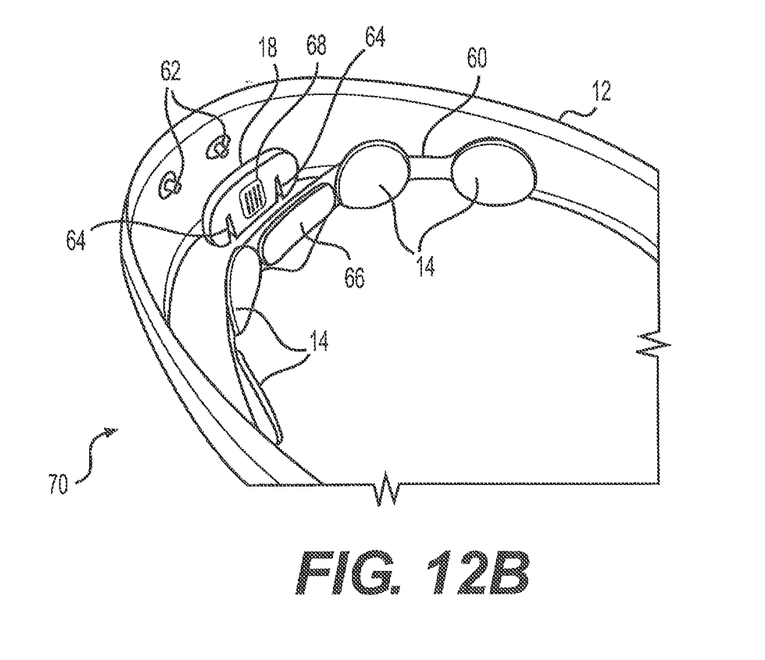

FIGS. 8-12B illustrate various views of an additional stimulator device, according to further aspects of the disclosure. The device 70 may be similar in function to device 10. In such a manner, device 70 may include band 12 (FIGS. 8, 12A, and 12B), electrodes 14, leads 16, and a stimulator 18. However, as shown, device 70 may include substrate 60. FIG. 8 is a view of device 70 positioned on a subject, while FIG. 9 illustrates device 70 with band 12 removed so as to illustrate additional components of device 70. FIG. 10 illustrates device 70 without band 12 or stimulator 18, while FIG. 11 illustrates substrate 60 including various printed components on substrate 60. FIGS. 12A and 12B are exploded perspective views of device 70. As noted above, substrate 60 may be made of mylar, polyester, or other suitable material. Substrate 60 may be suitability thin and flexible so as to conform to a portion of the subject's head (e.g., the forehead) and may optionally be adhesive. Electrodes 14 and leads 16 may be printed on the substrate 60, as noted above. In some examples, substrate 60 may include portions moveable with respect to other portions of substrate 60. That is, while substrate 60 is depicted as a monolithically formed one-piece construction, in other arrangements, the substrate may include a plurality of portions (e.g., two or more) coupled together (e.g., moveably coupled to one another, slidably coupled with respect to one another, etc.) through any appropriate means. In such an example, one or more of electrodes 14 and/or leads 16 may be printed on one portion of substrate 60 while one or more of electrodes 14 and/or leads 16 are printed on another portion of substrate. As such, spacing of electrodes 14 may be adjusted to accommodate a wide range of subject head sizes.

Further, as shown in FIG. 12B, substrate 60 may include a pad member 66. Pad member 66 may comprise one or more of a cushion or an adhesive member. Optionally, pad member 66 may be stretchable so as to accommodate preferred electrode 14 placement and different size subject heads. In addition, as shown in FIG. 9-12B, substrate 60 may include one or more coupling mechanisms 62 (e.g., posts 62) configured for coupling stimulator 18, including conductive portion 68, to substrate 60. Optionally, band 12 may include one or more coupling mechanisms 62 (e.g., posts 62) configured for coupling stimulator 18 to band 12. While posts 62 are depicted, the disclosure is not so limited. Instead, posts 62 may be supplemental to, or replaced by, any appropriate fastener such as, e.g., screws, snaps, nails, magnets, Velcro, and adhesives, etc. Posts 62 may cooperate (e.g., mate or correspond) with an appropriate coupling feature(s) 64 of stimulator 18. For example, coupling features 64 of stimulator 18 may include tapered channels. In use, stimulator 18 may be mounted to substrate 60 by positioning posts 62 in a first end (e.g., wider end) of coupling features 64 and moving stimulator 18 relative to substrate (e.g., downward)

such that posts 62 move toward a second end (e.g., narrow end) of coupling features 64. In such a manner, posts 62 may be received within coupling features 64 via an interference fit so as to secure stimulator 18 to substrate 60 and band 12. Accordingly, while two posts 62 and two coupling features 64 are shown, device 70 may include any appropriate number of coupling mechanisms 62 and coupling features 64 without departing from the scope of this disclosure. In yet a further arrangement, stimulator 18 may be fixedly (e.g., permanently) coupled to band 12. In the arrangement of FIGS. 8-12B, stimulator 18 may be coupled directly to substrate 60, within band 12, such that device 70 may be free from extraneous wires, components, and/or materials to increase ease and comfort of use by a subject. Additionally, upon coupling stimulator 18 to substrate 60, conductive portion 68 may be positioned in direct contact with the ends 71 of printed leads 16 and/or electrodes 14 for communication therebetween. As shown in FIG. 11, four leads 16, each terminating in an end 71 at a center of substrate 60, may be printed on substrate 60. Each lead 16 may be associated (e.g., in communication with) one of electrodes 14. Upon attachment of stimulator 18, ends 71 may contact conductive portion 68 of stimulator 18. Additionally, in some arrangements, band 12 may be reusable, while substrate 60 and electrodes 14 are disposable.

In use, a subject may remove electrodes 14 (and/or substrate 60) from packaging materials, peel away any liners or the like to expose adhesive portions, if any, of electrodes 14 and/or substrate 60, and attach (e.g., stick, couple, etc.) electrodes 14 and/or substrate 60 onto the forehead in a desired location. Gentle pressure may be applied, if necessary, to ensure electrodes 14 and/or substrate 60 are successfully adhered to the skin of the subject. Additionally, stimulator 18 may be coupled (e.g., via coupling mechanisms 62 and coupling features 64) to substrate 60 such that conductive portion 68 may communicate with leads 16 and/or electrodes 14. Additionally, the subject may maintain the position of one or more of electrodes 14 and/or substrate 60 with one hand, while stretching band 12 around substrate 60 and/or electrodes 14 with the other hand to hold substrate 60 and/or electrodes 14 firmly in place for use.

We claim:

1. A method of delivering transcranial stimulation, including:
   delivering a first transcranial stimulation to a subject via a plurality of electrodes;
   monitoring brain activity of the subject at least after delivery of the first transcranial stimulation;
   receiving feedback from the subject regarding a lucid dreaming experience that occurred during or after (1) delivery of the first transcranial stimulation to the subject via the plurality of electrodes and (2) monitoring brain activity of the subject at least after delivery of the first transcranial stimulation; and
   delivering a second transcranial stimulation to the subject via the plurality of electrodes, the second transcranial stimulation having a characteristic including at least one of a location, a frequency, an amplitude, a duration, or a timing of stimulation, wherein the characteristic is based on at least one of the monitored brain activity or the subject feedback regarding the lucid dreaming experience.

2. The method of claim 1, wherein delivering the second transcranial stimulation includes delivery of Transcranial Alternating Current Stimulation (tACS).

3. The method of claim 1, further including delivering visual or audio content relating to a topic prior to delivering the first transcranial stimulation.

4. The method of claim 3, wherein the delivered visual or audio content is subject-selected from a database.

5. The method of claim 4, wherein the database includes content associated with alternative subjects.

6. The method of claim 1, further including sensing whether the subject has entered a Rapid Eye Movement (REM) sleep period.

7. The method of claim 1, further including adjusting a location of at least one of the plurality of electrodes based upon the received subject feedback.

8. The method of claim 1, further including monitoring brain activity of the subject to determine whether a portion of the brain associated with dreaming has been stimulated to a predetermined level.

9. The method of claim 1, wherein delivering the second transcranial stimulation to the subject via the plurality of electrodes includes delivering a stimulation waveform including two or more frequencies simultaneously.

10. A method of delivering transcranial stimulation, including:
    positioning a plurality of electrodes on a forehead of a subject;
    sensing whether the subject is experiencing a Rapid Eye Movement (REM) sleep period; and
    delivering transcranial stimulation to the subject via the plurality of electrodes to induce or continue a lucid dream.

11. The method of claim 10, further including terminating delivery of transcranial stimulation to the subject based on sensing the subject is not in the Rapid Eye Movement (REM) sleep period.

12. The method of claim 10, wherein delivering transcranial stimulation to the subject includes delivering transcranial stimulation to the subject at a first frequency, the method further including:
    determining a change of frequency of brain activity of the subject from the first frequency towards a second frequency exhibited by a brain of the subject after ceasing delivery of transcranial stimulation at the first frequency.

13. The method of claim 12, further including delivering transcranial stimulation to the subject via the plurality of electrodes at the second frequency to induce or continue the lucid dream.

14. The method of claim 10, wherein delivering transcranial stimulation includes delivery of Transcranial Alternating Current Stimulation (tACS).

15. The method of claim 10, further including changing a characteristic of the transcranial stimulation based on one or more individual biological preferences of the subject.

16. The method of claim 15, wherein the individual biological preferences include at least one of a monitored brain frequency following terminating delivery of transcranial stimulation.

17. The method of claim 10, further including delivering visual or audio content relating to a topic prior to delivering transcranial stimulation.

18. The method of claim 10, further including receiving subject feedback and adjusting a location of at least one of the plurality of electrodes based upon the received subject feedback.

19. The method of claim 10, wherein delivering transcranial stimulation to the subject via the plurality of electrodes includes delivering a stimulation waveform including two or more frequencies simultaneously.

20. A method of delivering transcranial stimulation, including:
   positioning a plurality of electrodes relative to a head of a subject;
   delivering transcranial stimulation to the subject via at least one of the plurality of electrodes at a first frequency;
   ceasing delivery of transcranial stimulation at the first frequency;
   monitoring brain activity of the subject at least after ceasing delivery of transcranial stimulation at the first frequency via the at least one of the plurality of electrodes; and
   delivering transcranial stimulation to the subject via at least one of the plurality of electrodes at a second frequency, different than the first frequency, so as to induce or continue a lucid dream.

21. The method of claim 20, wherein positioning the plurality of electrodes includes positioning three electrodes relative to the head of the subject.

22. The method of claim 20, wherein positioning the plurality of electrodes includes positioning at least one electrode having a first shape or size and positioning at least a second electrode having a different shape or size than the first electrode.

23. The method of claim 20, wherein the steps of delivering transcranial stimulation at the first frequency and monitoring brain activity is performed via each of the plurality of electrodes.

24. The method of claim 20, wherein delivering at least one of transcranial stimulation at the first frequency or transcranial stimulation at the second frequency includes delivery of Transcranial Alternating Current Stimulation (tACS).

25. The method of claim 20, wherein delivering transcranial stimulation to the subject via the plurality of electrodes at at least one of the first frequency or the second frequency includes delivering a stimulation waveform including two or more frequencies.

26. A method of delivering transcranial stimulation, including:
   positioning a plurality of electrodes relative to a head of a subject at specified locations of a standardized 10-20 system of brain locations, wherein positioning includes positioning a first electrode at approximately the F4 or AF4 location, and positioning a second electrode at approximately the F3 or AF3 location;
   delivering transcranial stimulation to the subject via the plurality of electrodes at a first frequency;
   ceasing delivery of transcranial stimulation at the first frequency;
   determining a change of frequency of brain activity of the subject from the first frequency towards a second frequency exhibited by a brain of the subject, after ceasing delivery of transcranial stimulation at the first frequency; and
   delivering transcranial stimulation to the subject via the plurality of electrodes at the second frequency.

27. The method of claim 26, wherein determining a change of frequency of brain activity is performed via at least one of the plurality of electrodes.

28. The method of claim 26, wherein delivering at least one of transcranial stimulation at the first frequency or transcranial stimulation at the second frequency includes delivery of Transcranial Alternating Current Stimulation (tACS).

29. The method of claim 26, further including delivering visual or audio content relating to a topic prior to at least one of delivering transcranial stimulation at the first frequency or delivering transcranial stimulation at the second frequency, wherein the delivered visual or audio content is subject-selected from a database, wherein the database includes content associated with alternative subjects.

30. The method of claim 26, wherein positioning further includes positioning a third electrode at approximately an Fpz location.

* * * * *